(12) United States Patent
Liu et al.

(10) Patent No.: US 8,547,554 B2
(45) Date of Patent: Oct. 1, 2013

(54) METHOD AND SYSTEM FOR DETECTING MOISTURE IN NATURAL GAS

(75) Inventors: Xiaoyong Frank Liu, Wellesley, MA (US); Yufeng Huang, Peabody, MA (US); John McKinley Poole, Maynard, MA (US); Gary S. Parece, Belmont, MA (US); Anthony Kowal, Berlin, MA (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 13/211,821

(22) Filed: Aug. 17, 2011

(65) Prior Publication Data
US 2013/0044323 A1  Feb. 21, 2013

(51) Int. Cl.
*G01N 21/59* (2006.01)

(52) U.S. Cl.
USPC ............... 356/437; 356/432; 356/246

(58) Field of Classification Search
USPC .... 356/432–444, 246, 317–319; 250/339.13, 250/339.03, 343, 345; 422/83; 73/23.34, 73/24.02, 335.04
See application file for complete search history.

(56) References Cited

U.S. PATENT DOCUMENTS

| | | | | |
|---|---|---|---|---|
| 3,979,589 A * | 9/1976 | Sternberg et al. | ........... | 250/252.1 |
| 4,589,971 A * | 5/1986 | Mayeaux | ................... | 204/430 |
| 6,353,225 B1 * | 3/2002 | Strzoda et al. | ........... | 250/339.13 |
| 6,519,039 B1 * | 2/2003 | Morishita et al. | ............. | 356/437 |
| 6,552,792 B1 * | 4/2003 | Pilgrim et al. | ................. | 356/432 |
| 6,657,198 B1 | 12/2003 | May | | |
| 6,775,001 B2 * | 8/2004 | Friberg et al. | ................. | 356/437 |
| 7,064,329 B2 * | 6/2006 | Webber | ................... | 250/339.12 |
| 7,502,115 B2 * | 3/2009 | Patel et al. | ..................... | 356/437 |
| 7,586,094 B2 | 9/2009 | Liu et al. | | |
| 7,679,059 B2 | 3/2010 | Zhou | | |
| 7,728,978 B2 * | 6/2010 | Zhou et al. | ..................... | 356/437 |
| 2003/0080295 A1 | 5/2003 | Webber et al. | | |
| 2006/0263256 A1 * | 11/2006 | Koshel et al. | ................... | 422/83 |
| 2007/0081162 A1 * | 4/2007 | Roller et al. | .................. | 356/437 |
| 2008/0255769 A1 * | 10/2008 | Zhou et al. | ...................... | 702/24 |
| 2010/0089117 A1 | 4/2010 | Liu et al. | | |
| 2010/0091278 A1 * | 4/2010 | Liu et al. | ....................... | 356/318 |
| 2010/0180667 A1 * | 7/2010 | Bender et al. | ................ | 73/23.34 |

FOREIGN PATENT DOCUMENTS

| | | |
|---|---|---|
| EP | 1860425 A1 | 11/2007 |
| JP | 2002131228 A | 5/2005 |
| WO | 2005047872 A1 | 5/2005 |

OTHER PUBLICATIONS

Search Report from GB Application No. 1214393.9 dated Nov. 15, 2012.

* cited by examiner

*Primary Examiner* — Sang Nguyen
(74) *Attorney, Agent, or Firm* — Fletcher Yoder P.C.

(57) ABSTRACT

A system includes a moisture analyzer configured to detect moisture in natural gas. The moisture analyzer includes an absorption cell that encloses and conducts the natural gas. The moisture analyzer also includes a pressure control device that may reduce a pressure of the natural gas inside the absorption cell. The moisture analyzer includes a light emitting device that may transmit light through the natural gas inside the absorption cell, as well as a photodetector that may detect an intensity of the light transmitted through the natural gas and exiting the absorption cell.

20 Claims, 3 Drawing Sheets

METHOD AND SYSTEM FOR DETECTING MOISTURE IN NATURAL GAS

BACKGROUND OF THE INVENTION

The subject matter disclosed herein relates generally to spectroscopy, and more particularly, to absorption spectroscopy for detection of moisture in natural gas.

Absorption spectroscopy based moisture analyzers exist for determining moisture concentration in a sample gas. However, determination of the concentration of moisture (i.e., water vapor), in natural gas may be complicated. For example, spectral interference between moisture and background gas (i.e., natural gas minus moisture) may be severe enough to pose a challenge to achieve desired sensitivity or accuracy in determining the concentration of moisture in natural gas.

Differential spectroscopy may be employed to reduce the spectral interference from background gas to determine the concentration of moisture in natural gas. One example of a process used in differential spectroscopy may include recording a spectrum of the background gas, which is essentially dried natural gas, subtracting this spectrum from a spectrum of natural gas to yield a differential spectrum, and determining the moisture concentration based upon the differential spectrum. However, this process requires a gas purifier and other requisite accessories to remove moisture from natural gas to record the background spectrum, which may be costly. Additionally, this process requires a switch between the sample gas to be analyzed (i.e., natural gas) and the reference gas (i.e., gas dried by the purifier, which is representative of the background gas), which may slow the system response time.

Moreover, there is no guarantee that the spectral interference would be effectively removed because the spectra of the sample gas and the background gas are not recorded at the same time and/or the chemical composition of background gas may vary over time, and, thus, its spectrum may vary over time. Accordingly, an approach that adequately addresses present issues regarding detecting moisture in natural gas is desirable.

BRIEF DESCRIPTION OF THE INVENTION

Certain embodiments commensurate in scope with the originally claimed invention are summarized below. These embodiments are not intended to limit the scope of the claimed invention, but rather these embodiments are intended only to provide a brief summary of possible forms of the invention. Indeed, the invention may encompass a variety of forms that may be similar to or different from the embodiments set forth below.

In one embodiment, a system includes a moisture analyzer configured to detect moisture in natural gas, which includes an absorption cell enclosing and conducting the natural gas, a pressure control device configured to reduce a pressure of the natural gas inside the absorption cell, a light emitting device configured to transmit light through the natural gas inside the absorption cell, and a photodetector configured to detect an intensity of the light transmitted through the natural gas and exiting the absorption cell.

In another embodiment, a method includes reducing a pressure of natural gas by a pressure control device to generate de-pressurized natural gas at a pressure lower than an ambient pressure of the natural gas, transmitting a light through the de-pressurized natural gas at a pre-selected wavelength or across a wavelength range, recording a spectrum of the de-pressurized natural gas, and determining a concentration of moisture in the natural gas based on the spectrum of the natural gas.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION OF THE INVENTION

One or more specific embodiments of the present invention will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements.

As discussed below, the disclosed embodiments relate to the application of a spectral linewidth reduction method, and a system based on such a method, to improve the detection of moisture in natural gas, including but not limited to LNG (liquefied natural gas) feed gas and regasified LNG. The system and method may also eliminate or reduce the spectral interference from background gas (i.e., dried natural gas) when detecting moisture in natural gas. In particular, the disclosed embodiments reduce sample gas pressure to reduce the overall spectral linewidth for a sample gas (i.e., natural gas). This reduction in the overall spectral linewidth for a sample gas lowers background gas interference and enables more sensitive and more accurate detection of moisture in natural gas. That is, the disclosed embodiments reduce a sample gas pressure without having to comprise on response time, or deconvolute moisture and background gas absorption, since a single spectrum of a natural gas sample may be utilized to determine the concentration of moisture in the natural gas sample.

Figure 1:
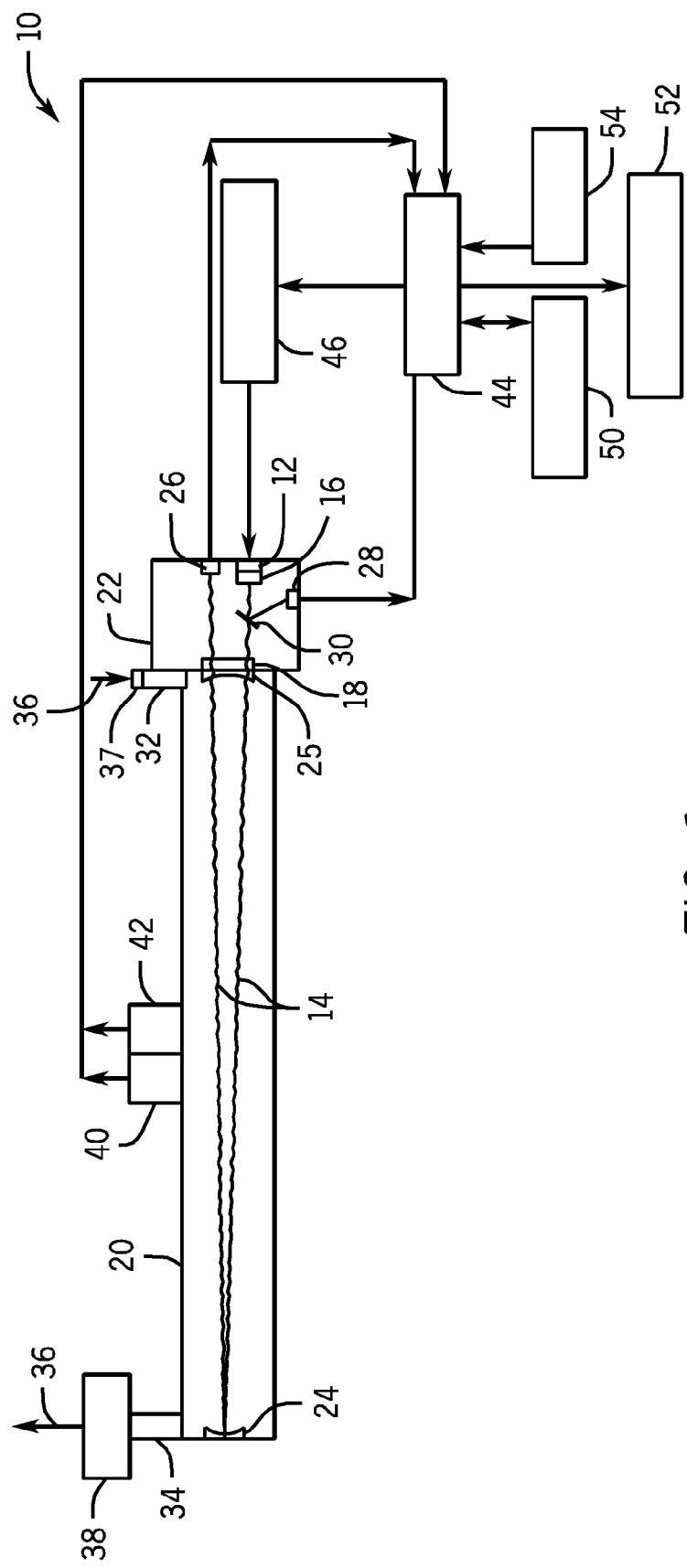
FIG. 1 is a block diagram of a tunable diode laser absorption spectrometer in accordance with an embodiment of the present technique.

Turning now to the drawings and referring first to FIG. 1, an embodiment of a wavelength-modulation spectroscopy analyzer 10 is illustrated. This analyzer 10 may generally detect moisture in a gas, such as natural gas. The analyzer may include, for example, a light emitting device 12. The light emitting device 12 may include, for example, a laser, a diode laser, a quantum cascade laser, or another light source. The light emitting device 12 may emit, for example, light at one or more particular wavelengths and at one or more particular modulation frequencies, which may be determined, for example, by a user. In one embodiment, the light emitting device 12 is a laser and may operate to transmit light at a single wavelength at a time. In another embodiment, the wavelength can be swept across a certain range and modulated at a certain frequency.

The light emitted by the light emitting device 12 may include a monochromatic radiation 14 that may pass through a collimator 16 that operates to collimate the monochromatic radiation 14. The collimated monochromatic radiation 14 may be transmitted to and through an optical window 18, so that the monochromatic radiation 14 may be transmitted into an absorption cell 20 (e.g., an enclosure). In this manner, monochromatic radiation 14 may pass from a chamber 22 into the absorption cell 20 while gases present, for example, in the absorption cell 20, may be prevented from entering the chamber 22.

In one embodiment, the absorption cell 20 may be a multipass absorption cell that enables the monochromatic radiation 14 to be reflected between a reflective element 24 (e.g., a minor) at one end of the absorption cell 20 opposite of the window 18, and another reflective element 25 (e.g., a second mirror) at the other end of the absorption cell 20, before exiting the absorption cell 20 through the window 18 and into the chamber 22. The monochromatic radiation 14 may then be detected by a photodetector 26. In this manner, the photodetector 26 may operate to detect an intensity of monochromatic radiation 14 exiting the absorption cell 20. In one embodiment, the light emitting device 12 may be provided by a laser diode integrated with a thermoelectric cooler (TEC), a temperature sensor, and a built-in photodetector that can detect the intensity of backward emission from the laser diode.

In another embodiment, an external reference photodetector 28 can be employed in addition to, or instead of, the built-in photodetector. As illustrated in FIG. 1, a beam splitter 30 may be utilized to split the monochromatic radiation 14. The beam splitter 30 may receive the monochromatic radiation 14 and may direct a portion of the monochromatic radiation 14 to the reference photodetector 28, and may enable the rest of the monochromatic radiation 14 to transmit through the absorption cell 20. In one embodiment, use of the reference photodetector 28 may be desirable in spectroscopy applications where a light emitting device 12 with a built-in photodetector is not readily available for a desired monochromatic radiation wavelength, where an external reference photodetector 28 is preferred, or where it is desirable to monitor the concentration of an analyte leaking into the chamber 22.

Additionally, the analyzer 10 may include an inlet 32 and an outlet 34 coupled to the absorption cell 20. The inlet 32 may operate to conduct a gas flow 36 into the absorption cell 20, while the outlet may operate to conduct the gas flow 36 out of the absorption cell 20. In one embodiment, this gas flow 36 may include natural gas. The gas flow 36 may be LNG feed gas, regasified LNG, substitute natural gas, or syngas. The inlet 32 may receive the gas flow 36 and may transmit the gas flow 36 into the absorption cell 20, where the gas flow 36 may be analyzed for moisture content. Additionally, the gas flow 36 may be de-pressurized by a pressure control device 38 downstream of an outlet 34 to enable more sensitive and more accurate detection of moisture in natural gas.

The pressure control device 38 may be, for example, a vacuum pump, an aspirator, or another de-pressurizing device, which may operate to reduce the pressure of the gas flow 36 from, for example, one standard atmosphere to a pressure substantially lower than one standard atmosphere, with assistance from a gas flow limiting device 37 upstream of the inlet 32. The gas flow limiting device 37 may include any known element able to restrict the gas flow 36, such as an orifice with a diameter less than the diameter of a conduit used to conduct gas flow 36. The pressure control device 38 may reduce the pressure of the gas flow 36 to approximately, 8 psia (pounds per square inch absolute), 7.5 psia, 7 psia, 6.5 psia, 6 psia, 5.5 psia, 5 psia, 4.5 psia, 4 psia, 3.5 psia, 3 psia, 2.5 psia, 2 psia, 1.5 psia, 1 psia, or 0.5 psia or between approximately 1 psia and 5 psia.

The analyzer 10 may also include one or more sensors such as a pressure sensor 40 and/or a temperature sensor 42. The pressure sensor 40 may acquire pressure measurements of the gas flow 36, while the temperature sensor 42 may acquire temperature measurements of the gas flow 36. These measurements may be provided to electronic circuitry 44. The electronic circuitry 44 may include one or more processors that may be digital signal processors, microprocessors, field-programmable gate arrays, complex programmable logic devices, application specific integrated circuits, and/or other logic circuitry. The electronic circuitry 44 may receive signals from the photodetector 26, the reference photodetector built into the light emitting device 12 (and/or the external reference photodetector 28), the pressure sensor 40, and the temperature sensor 42. The electronic circuitry 44 may utilize these signals to analyze and determine analyte concentration in the gas flow 36, such as the concentration of moisture in, for example, natural gas, based on the measured spectrum, pressure, and temperature of the gas flow 36. Additionally, the electronic circuitry 44 may also command a drive circuit 46 of the light emitting device 12. In one embodiment, the analyzer 10 may further include a display 52, an input device 54, and one or more I/O interfaces 50.

In one embodiment, the analyzer 10 may utilize absorption spectroscopy to determine the concentration of moisture of in the gas flow 36. The methods of absorption spectroscopy may include, but are not limited to, direct absorption spectroscopy, harmonic/derivative spectroscopy, photoacoustic spectroscopy, cavity ring down spectroscopy, and fluorescence spectroscopy. Spectral interference between, for example, moisture and the background gas in the gas flow 36, may be primarily caused by coincidental yet inherent adjacency between the transition frequencies of moisture and the background gas. However, the wavelength of the monochromatic radiation 14 emitted by the light emitting device 12 may be chosen to avoid such coincidental adjacency and minimize the spectral interference from the background gas. Moreover, through the use of the gas flow 36 limiting device 37 and the pressure control device 38, the pressure of the gas flow 36 may be reduced, leading to reduced spectral linewidth and, thus, reduced spectral interference between, moisture and the background gas in the gas flow 36.

Figure 2:
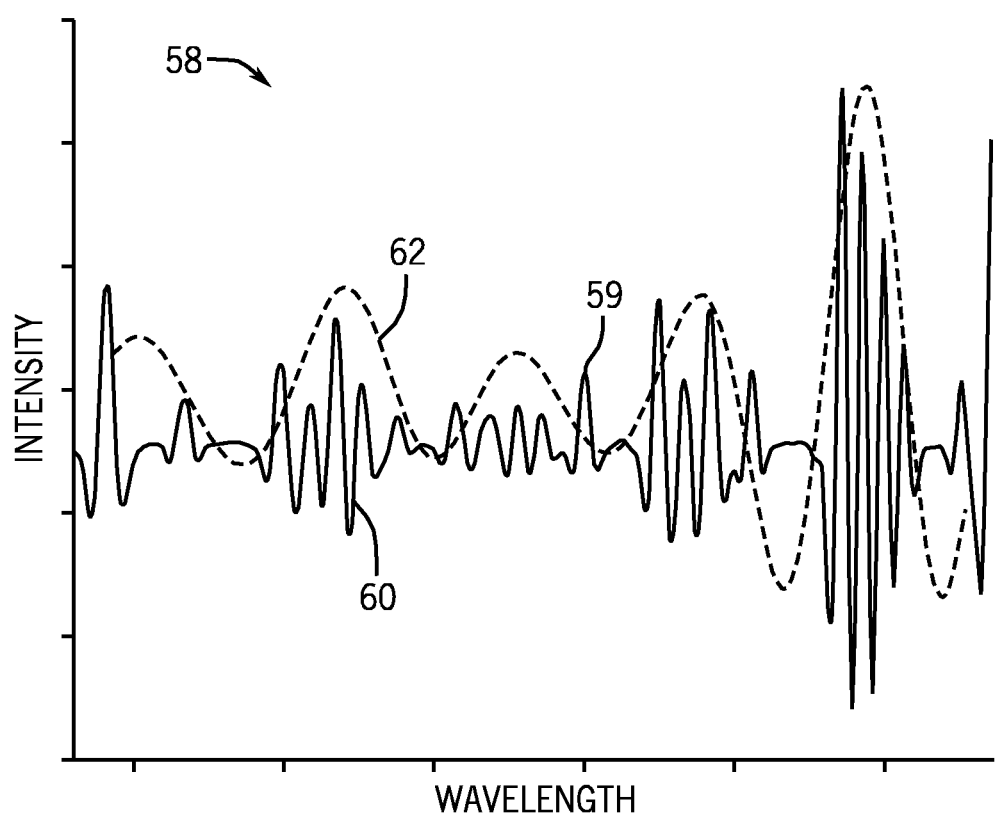
FIG. 2 is a chart illustrating of an example of a second harmonic spectrum of natural gas by a spectrometer of FIG. 1 in accordance with an embodiment of the present technique.

FIG. 2 illustrates a chart 58 that details a second harmonic (2f) spectrum 60 for a gas flow 36 (e.g., natural gas) at a reduced pressure (e.g., 2.5 psia, 5 psia, or 8 psia) containing a certain level of moisture content when exposed to the monochromatic radiation 14 across a range of wavelengths. Also illustrated in chart 58 is another 2f spectrum 62 for a gas flow 36 (e.g., natural gas) when exposed to the monochromatic radiation 14 across a range of wavelengths at an ambient pressure while containing the same level of moisture content as gas flow 36 at the reduced pressure (i.e., the same level of moisture content present in the gas flow 36 for the 2f spectrum 60). As illustrated in chart 58, at ambient pressure, the 2f spectrum 62 is poorly resolved due to line broadening along the wavelength axis, the spectral lines are clumped together, and the targeted spectral line of moisture 59 is barely visible. In contrast, the 2f spectrum 60 is well resolved along the wavelength axis, revealing fine details that would otherwise be missing, including the targeted moisture line 59. Thus, chart 58 illustrates that de-pressurizing the gas flow 36 may enable the analyzer 10 to attain superior detection selectivity, accuracy, and sensitivity for the detection of moisture present in the gas flow 36.

Figure 3:
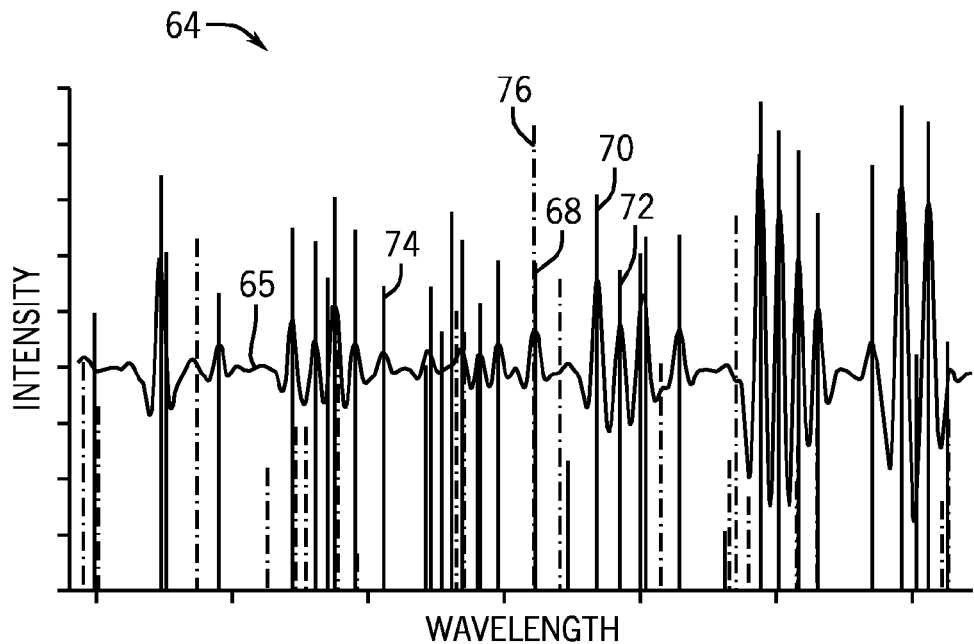
FIG. 3 is a chart illustrating of an example of another second harmonic spectrum of natural gas by a spectrometer of FIG. 1 in accordance with another embodiment of the present technique.

However meticulously the wavelength, or wavelength range, of a monochromatic radiation 14 is chosen, it is difficult to avoid altogether coincidental adjacency in spectral line positions, as the line positions are inherent and dictated by the molecular structures of species present in the gas flow 36. FIG. 3 illustrates a chart 64 that manifests such a difficulty. In chart 64, the smooth curve 65 illustrates a 2f spectrum of dry methane ($CH_4$) recorded at a reduced pressure (e.g., 2.5 psia, 5 psia, or 8 psia), the concentration of which is typically above 90% in natural gas. The solid straight lines in chart 64 are the spectral lines attributed to methane, including lines 68, 70, 72, and 74. The dashed straight lines in chart 64 are the spectral lines attributed to moisture, including the targeted line 76, which is used to detect moisture present in the gas flow 36.

As illustrated in chart 64, methane line 68 overlaps with moisture line 76 in wavelength. The ratio between methane line 68 and one or more of methane lines 70, 72 and 74 is spectroscopically inherent with methane, is a function of relative spectral intensity, gas pressure and temperature, and can be accurately calculated. In one embodiment, the analyzer 10 may be configured to calculate a methane baseline underlying the targeted moisture line, based on real-time detection of one or more of methane lines 70, 72, and 74, and based on a predetermined ratio between methane line 68 and one or more of methane lines 70, 72, and 74, 76, so that the methane baseline may be subtracted from a composite of the targeted moisture line 76 and the overlapping methane line 68, to determine the exact concentration of moisture in the gas flow 36.

Figure 4:
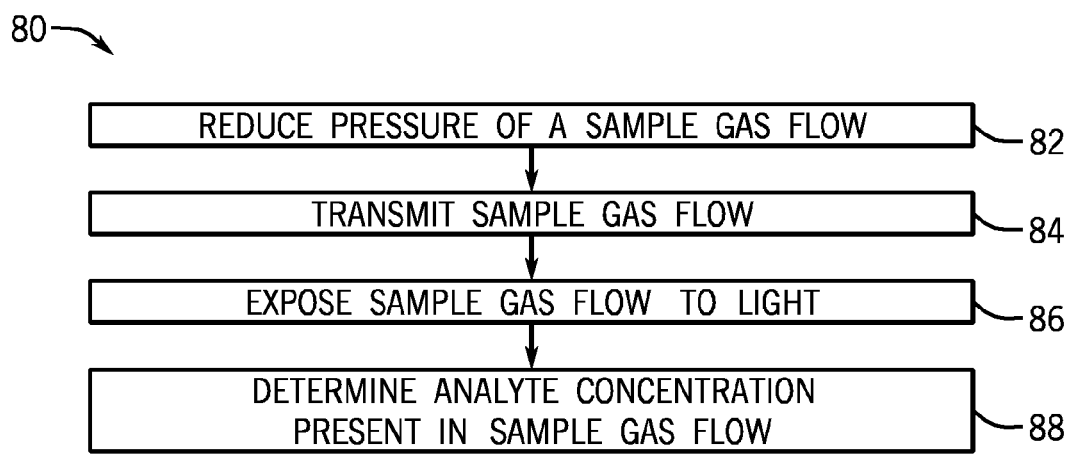
FIG. 4 is flow chart illustrating a process for performing spectral analysis with a spectrometer of FIG. 1 in accordance with an embodiment of the present technique.

FIG. 4 illustrates a flow chart 80 describing one embodiment for the detection of an analyte concentration in a gas flow 36, including, for example, a concentration of moisture in a sample gas such as natural gas or syngas. In step 82, the pressure of the sample gas flow 36 may be reduced by, for example, a pressure control device 38 alone, or in combination with a flow limiting device 37. In step 84, the de-pressurized gas flow 36 is transmitted through an absorption cell 20. In step 86, the de-pressurized gas flow 36 is exposed to light from a light emitting device 12 inside the absorption cell 20. In step 88, the concentration of an analyte (e.g., moisture) in the sample gas flow (e.g., natural gas) is determined based on an absorption-based spectrum of the de-pressurized gas flow 36.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A system, comprising:
    a moisture analyzer configured to detect moisture comprising water present in natural gas, comprising:
        an absorption cell enclosing and conducting the natural gas;
        a pressure control device configured to reduce a pressure of the natural gas inside the absorption cell to generate de-pressurized natural gas at a pressure lower than an ambient pressure of the natural gas;
        a light emitting device configured to transmit light through the de-pressurized natural gas inside the absorption cell; and
        a photodetector configured to detect an intensity of the light transmitted through the de-pressurized natural gas and exiting the absorption cell.

2. The system of claim 1, comprising electronic circuitry configured to acquire and process a spectrum of the natural gas.

3. The system of claim 2, wherein the electronic circuitry is configured to determine a concentration of moisture in the natural gas based on the spectrum.

4. The system of claim 2, wherein the electronic circuitry is configured to subtract a background value from a spectral feature within the spectrum of the natural gas based on a predetermined ratio to determine a concentration of moisture in the natural gas.

5. The system of claim 2, wherein the spectrum comprises an absorption-based spectrum.

6. The system of claim 2, wherein the spectrum comprises a direct absorption spectrum.

7. The system of claim 2, wherein the spectrum comprises a derivative spectrum.

8. The system of claim 2, wherein the spectrum is based on photoacoustic spectroscopy.

9. The system of claim 2, wherein the spectrum is based on cavity ring down spectroscopy.

10. The system of claim 2, wherein the spectrum is based on fluorescence spectroscopy.

11. The system of claim 1, wherein the light emitting device comprises a laser, a diode laser, or a quantum cascade laser.

12. The system of claim 11, wherein the diode laser comprises:
    a thermoelectric cooler;
    a temperature sensor; and
    a built-in photodetector configured to detect an intensity of backward emission from the diode laser.

13. The system of claim 1, wherein the pressure control device comprises a vacuum pump or an aspirator.

14. The system of claim 1, wherein the pressure control device is configured to reduce the pressure of the natural gas to between approximately 1 psia and 5 psia.

15. The system of claim 1, wherein the natural gas comprises pipeline natural gas, liquified natural gas feed gas, or regasified liquefied natural gas.

16. The system of claim 1, wherein the absorption cell comprises a multipass absorption cell.

17. A method, comprising:
    reducing a pressure of natural gas by a pressure control device to generate de-pressurized natural gas at a pressure lower than an ambient pressure of the natural gas;

transmitting a light through the de-pressurized natural gas at a pre-selected wavelength or across a wavelength range;

recording a spectrum of the de-pressurized natural gas; and determining via electronic circuitry a concentration of moisture comprising water present in the natural gas based on the spectrum of the natural gas.

18. The method of claim 17, comprising reducing the pressure of the natural gas to generate de-pressurized natural gas at a pressure of no more than approximately 5 psi.

19. The method of claim 17, comprising reducing the pressure of the natural gas to generate de-pressurized natural gas at a pressure of no more than approximately 2.5 psi.

20. The method of claim 17, wherein the concentration of moisture is determined by subtracting a background value from a spectral feature within the spectrum of the de-pressurized natural gas based on a predetermined ratio.

* * * * *